Figure 1:
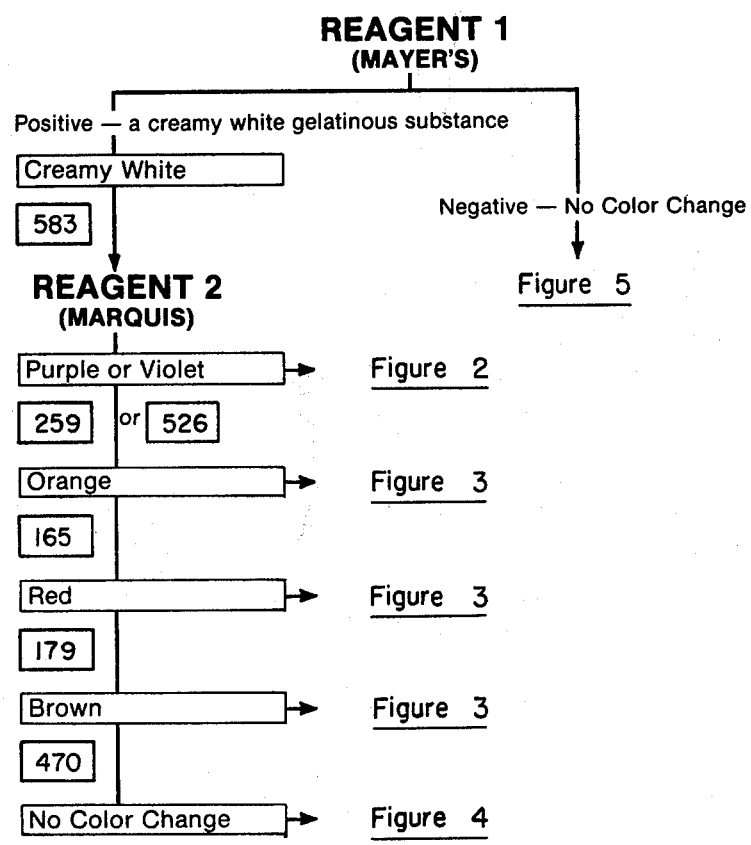

United States Patent [19]

Carroll

[11] 4,104,027

[45] Aug. 1, 1978

[54] PROCESS FOR THE PRESUMPTIVE IDENTIFICATION OF NARCOTICS AND DRUGS OF ABUSE

[76] Inventor: Robert B. Carroll, P.O. Box 305, S. Paris, Me. 04281

[21] Appl. No.: 853,682

[22] Filed: Nov. 21, 1977

[51] Int. Cl.$^2$ .......................................... G01N 33/16
[52] U.S. Cl. .................................................. 23/230 B
[58] Field of Search ...................................... 23/230 B

[56] References Cited

U.S. PATENT DOCUMENTS

| | | | |
|---|---|---|---|
| 3,656,906 | 4/1972 | Bullock | 23/230 B |
| 3,713,779 | 1/1973 | Sirago et al. | 23/230 B X |
| 3,761,227 | 9/1973 | Conrad et al. | 23/230 B |
| 3,873,270 | 3/1975 | Hamilton et al. | 23/230 B |
| 3,955,926 | 5/1976 | Fischer | 23/230 B |

Primary Examiner—Robert M. Reese

[57] ABSTRACT

A process is provided for the presumptive identification of narcotics and drugs of abuse, utilizing a combination of color-producing reagents in a sequence which minimizes the occurrence of false positives, and makes possible the presumptive identification by color matching of virtually all the important narcotics and drugs of abuse found in traffic at the present time.

6 Claims, 5 Drawing Figures

PROCESS FOR THE PRESUMPTIVE IDENTIFICATION OF NARCOTICS AND DRUGS OF ABUSE

In order to obtain sufficient evidence to detail a suspected drug peddler or drug user, it is very important for the law enforcement authorities to be able to quickly identify materials suspected of being narcotics or drugs of abuse. The quickest test known for drug identification is a color test, in which the response of the drug to a specified reagent makes it possible to assign the drug to one or more classes. Accordingly, a combination of such color tests should make it possible to eliminate other substances falling in the same category and presumptively identify the drug in question.

The presumptive identification of a drug using a single color test is virtually impossible. Clark, *Isolation and Identification of Drugs*, Pharmaceutical Press (1969), lists some 59 drugs that all respond in the same way to Marquis reagent, a test for the identification of the opium alkaloids, and thus appear as opium alkaloids.

At least thirty different drugs respond to cobalt thiocyanate reagent in the same matter as cocaine, including phendimetrazine and diethyl proprion, and thus, although not cocaine or a derivative of cocaine, would nonetheless be identified as cocaine.

Mandelin's reagent, the color-producing reagent used to identify the amphetamines, gives more or less the same color with a large number of nonamphetamines, such as Anacin, aspirin, Excedrin, Darvon (d-proproxyphene), promethazine, D-lysergic acid, and benzocaine.

Ehrlich's reagent responds to LSD and the ergot alkaloids to form a purple color. However, since the color is imparted by the indole structure, a similar reaction can be obtained with milk powder, wheat germ, serum, tryptophane, and any other compound containing the indole nucleus.

It is thus apparent that single color-producing reagents cannot really serve for the field identification of drugs, because of the possibility of giving a false positive with other substances of similar structure or similar response characteristics. Accordingly, reagents which are being marketed as specific reagents for the identification of various drugs are actually misnamed.

One composition being marketed as a specific reagent for PCP (phencyclidine hydrochloride) is composed of ammonium hydroxide and cobalt thiocyanate, to be used together. While PCP gives a blue color with this reagent so also do heroin, tetracaine, Darvon (d-propoxyphene), methadone, Dormin (methapyrilene). Promazine, Promethazine, Chloropromazine and Dibucaine.

Another specific reagent combination for PCP that is being marketed is composed of a first reagent, xylene acidulated with an organic acid, and a second reagent, cobalt thiocyanate, formulated with 1:1 glycerine and water. The color formation in cobalt thiocyanate is supposedly partitioned into the acidulated xylene, to make it "specific" for PCP but the reagent in fact gives a similar set of color responses with drugs other than PCP.

Another reagent being marketed as specific for cocaine consists of a three part reagent called "Scott Reagent". The first part of this reagent is also a mixture of cobalt thiocyanate in a 1:1 glycerine-water solution. The second part of the reagent is concentrated hydrochloric acid, to decolorize the blue complex, while the third part is comprised of chloroform, which forms a bright blue solution in the presence of cocaine and other compounds. The purpose of the solvent mixture is to slow the formation of the color complex in many of the drugs and other chemicals forming a blue complex with cobalt thiocyanate similar to that formed with cocaine. This it does to some degree, but not enough to separate the false positives.

Another specific reagent being marketed is a concentrated solution of sodium hydroxide in methanol. A drop or two of this material hydrolyzes the benzoate part of the cocaine molecule, and in the presence of the methanol forms methyl benzoate, which has an odor similar to wintergreen. However, any benzoate compound will produce the same odor, and the salicylates would produce the odor of wintergreen, since this is the compound formed upon transesterification of salicylates.

The weakness of the single specific reagent tests has led to the development of various combination tests, which are intended to be used together in a manner which seeks to screen out the false positives, and make possible a firm identification of nearly all of the available drugs and narcotics. Velapoldi and Wicks, *Journal of Forensic Sciences*, Vol. 19, No. 3, pages 636–656 (1974) provide a group of seven reagents used in a reasonable multireagent testing scheme which would decrease the number of false positives and increase specificity. They also sought to standardize the colors produced with these reagents, and develop the colors from a spot plate technique, mixing a crystal or two of drug with a microdrop or two of reagent, examining the color so produced by a split field, and comparing the color with the chips of lacquer available in the ISCC-NBS Centroid Color Charts.

However, their proposals have proved to have serious limitations. The available colors on these charts are limited to some 260 variations, and thus do not in many cases provide a color matching the color produced by the color producing reagent. Moreover, sample size is a function of color response. Some drugs produce a very intense color response, propoxyphene with Marquis reagent will form a purple color that is so intense as to be virtually black. With other drug combinations, a low level of drug will produce no color, and unless a larger amount of drug is used, a negative response may be recorded.

Figure 4:
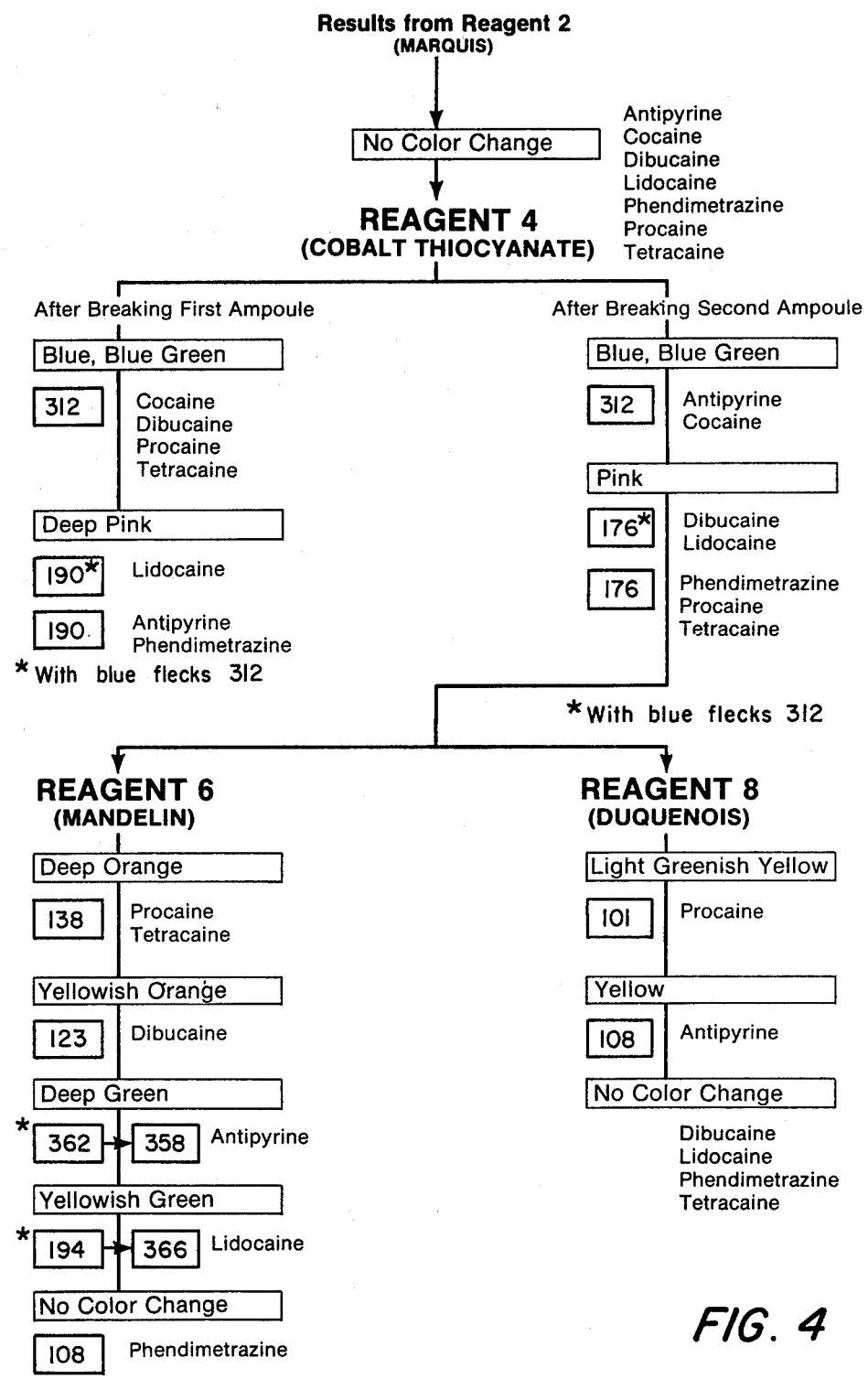

For example, in FIG. 4, page 652 of the report indicates that neither cocaine nor quinine produce a color in Mandelin Reagent. In fact when sample sizes are from 1–5 mgm with 0.5 ml of reagent, cocaine produces a reddish-orange color while quinine forms a lime green color with Mandelin Reagent. Different colors may be produced if the proportions are outside these ranges.

A further difficulty is that the color that is formed depends upon the time after mixing with the color producing reagent. Transient colors or color sequences are obtained. Many reagents such as Marquis reagent, Mecke's reagent and Mandelin's reagent contain strong solutions of sulfuric acid, which attacks the compound to produce a charred black or brownish black color with time.

The test procedure that they proposed utilizes Marquis reagent as the initial reagent, for determining the first sequential test series. Those drugs giving a purple violet black color with Marquis reagent were then tested further using either nitric acid (A-9) or Mandelin Reagent (A-6). However, these tests sometimes could not distinguish between two drugs, leaving positive identification uncertain. Moreover, Darvon forms a yellow color slowly in nitric acid (A-9), which is not referred to in the chart, and would result in placing it as heroin, making it impossible to separate it later by Mandelin Reagent (A-6).

Figure 3:
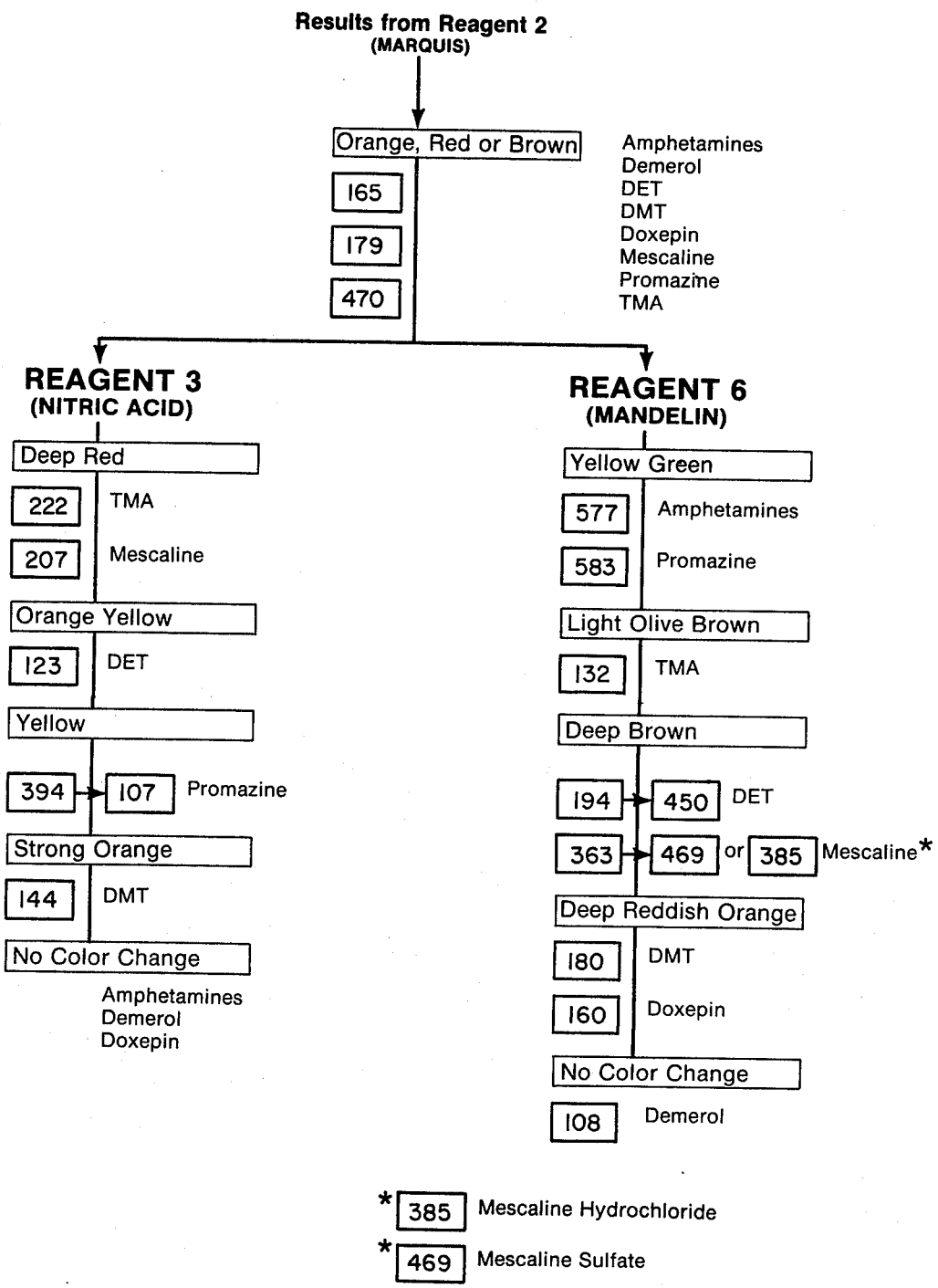

The absence of a time period for comparison of the color after addition of the color-producing reagent is responsible for placing aspirin and PCP together in the same pink red response in FIG. 3, page 651 of the same report. Aspirin takes approximately 5 minutes to turn pink, and additional time to reach a cherry red color, while PCP forms a lavender, not a pink color, in Marquis reagent within one minute. Dilantin (phenytoin) and theophylline give the same color as barbituates in Dille-Koppanyi Reagent (A-2), but the barbiturates do not turn tan in Marquis reagent; they are colorless, as is theophylline. The reagent itself turns tan on long exposure to air. Failure to take into account sample size effects on color formation, the time required for the formation of the color, and the limitations in the number of colors available for comparison with the color code, all weaken the usefulness of the method, and the test sequences described.

Another narcotics identification system being marketed indicates that, with Marquis reagent, demerol hydrochloride gives an orange color changing to olive-green, whereas the orange remains for at least 10 to 15 minutes. If one did not wait long enough to observe this change, one is instructed to test with nitric acid for either mescaline or methedrine. With nitric acid, demerol is practically colorless and could be called colorless or a very pale yellow. If read as a pale yellow one is instructed to stop testing as no drug is indicated. If read as "no color", one is instructed to next test with the reagent for opiates, where demerol responds as yellow-orange changing to brown, the same color response that is assigned to methedrine. When run side by side, both methedrine and demerol produce the same colors with this reagent, but methedrine makes its color change from orange to brown just slightly faster than does demerol. The instructions, then direct one to test the substance with a reagent for brown heroin; here a pale yellow is formed with demerol of sufficient intensity to be seen as a pale yellow and one is directed to stop further testing as no drug was detected. However, if one read the response as "no color", one would have presumptively identified methedrine rather than demerol.

DMT (N,N-dimethyl tryptamine) is shown as giving a yellowishgreen color with Marquis reagent. In fact, the color is a pale orange that slowly turns to olive, suggesting demerol or MMDA. One is instructed to test with the reagent for brown heroin next but in this test DMT forms a yellow color that changes to olive green. One is instructed to stop testing as no drug has been detected. If one did not wait long enough to observe the initial change from orange to olive, with Marquis reagent, the instructions direct one to test next with nitric acid. This reagent forms a strong orange color with DMT and the instructions direct one to stop testing as no drug has been detected.

Benactyzine hydrochloride with Marquis reagent gives an orange color changing to blue. One is instructed to next test the substance with nitric acid where no color is formed. One is next directed to test the substance with the reagent for opiates which forms a blue color. Next one is directed to the reagent for brown heroin where benactyzine forms a brilliant deep orange, which turns, in 15 to 20 seconds, to a deep olive green. Based on this color change on is directed to stop testing as no drug was detected.

Mescaline hydrochloride with Marquis reagent gives not an orange color staying orange, as does methedrine, but red, while the color produced with methedrine is an orange that changes to a deep reddishorange and then finally, after a few minutes, to a deep brown. Red is not shown for mescaline and thus one would be unable to test for this drug.

Methadone with Marquis reagent turns orange, which deepens to an orange-brown. This suggests amphetamines or TMA rather than methadone. Quinine with Marquis reagent turns a pale tan, which would be read as suggesting amphetamines or TMA but testing for these would cause one to conclude one had methedrine rather than methadone or quinine.

Phencyclidine hydrochloride (PCP) with Marquis reagent, if this drug is pure, gives a pale lavender. This might possibly be read as no color, since it is so very pale. This leads one to test with Scott reagent as for cocaine, where one would obtain a pale blue color with a pink solution over it (two layers), which implies cocaine, not PCP.

A test sequence utilizing Mayer's reagent as the first test reagent has been in use since 1969 for the presumptive identification of narcotics, hallucinogens and dangerous drugs. Mayer's reagent gives a positive response with opium, coca alkaloids and amphetamines, so that a negative response immediately eliminates these drugs from further consideration. In the case of a positive response to Mayer's reagent, Marquis reagent is next used. This reagent turns purple or violet in the presence of most of the opium alkaloids, and an orange or red in the presence of the amphetamines, as well as several other drugs. Where a purple or violet color occurs with Marquis reagent nitric acid can be used to separate two of the opiates, morphine and heroin. Morphine rapidly changes from an initial orange to a deep red color with nitric acid, and then after a minute or two turns to a light orange. Heroin on the other hand turns nitric acid a light yellow color. The use of a small amount of reagent and a small amount of heroin gives an apple green color that is formed slowly, but this color is not formed with the larger amounts of reagent and drug presently used in test procedures. This sequence is not however adequate to distinguish among the wide variety of drugs and mixtures of drugs that have come to be used in recent years by the drug culture.

In accordance with the invention, a process is provided for the presumptive identification of narcotics and drugs of abuse, based on a test sequence starting with Mayer's reagent, standardizing sample and reagent size as well as the time for color response and the color produced, utilizing as the standard for comparison the Pantone color matching system, with reference to the colors shown on uncoated paper.

The Pantone Color Specifier and the *Pantone Color & Black Selector* are each dictionaries of colors. Each color is assigned a number, this number is printed on each of the convenient tear-out chips, insuring faithful color identification. Accordingly, each color obtained in each test in the test sequence of the invention is assigned a Pantone color number in one of these reference dictionaries for reference purposes. The *Pantone Color Specifier* and the *Pantone Color & Black Selector* are published by Pantone Inc., Moonachie, New Jersey 07074, and specific reference is made to the 1973 Edition of the *Pantone Color Specifier* and to the 1970 edition of the *Pantone Color & Black Selector*.

The use of Mayer's reagent as the first screening reagent and Marquis reagent as the second screening reagent removes from testing with Marquis reagent those components which would become false positives for one or more of the primary drugs being presumptively identified in the charts shown in the accompanying drugs. If Marquis reagent were used first, D-lysergic acid for example by its response to Marquis reagent would be next tested with nitric acid, where it could be confused with one or more of the opium alkaloids. Doriden (glutethemide) and methadone by their response to Marquis reagent would next be tested with and would also give a confusing response to Mandelin reagent. The barbiturates, benzocaine and methprylon would by their response to Marquis reagent next be tested with cobalt thiocyanate, and would become false positives for the drugs separated by this reagent, and methypryllon would be difficult to separate from antipyrine in Mandelin reagent, because the colors are similar. LSD (lysergic acid diethyl amide) could be mistaken for promazine in its reaction to nitric acid.

Figure 2:
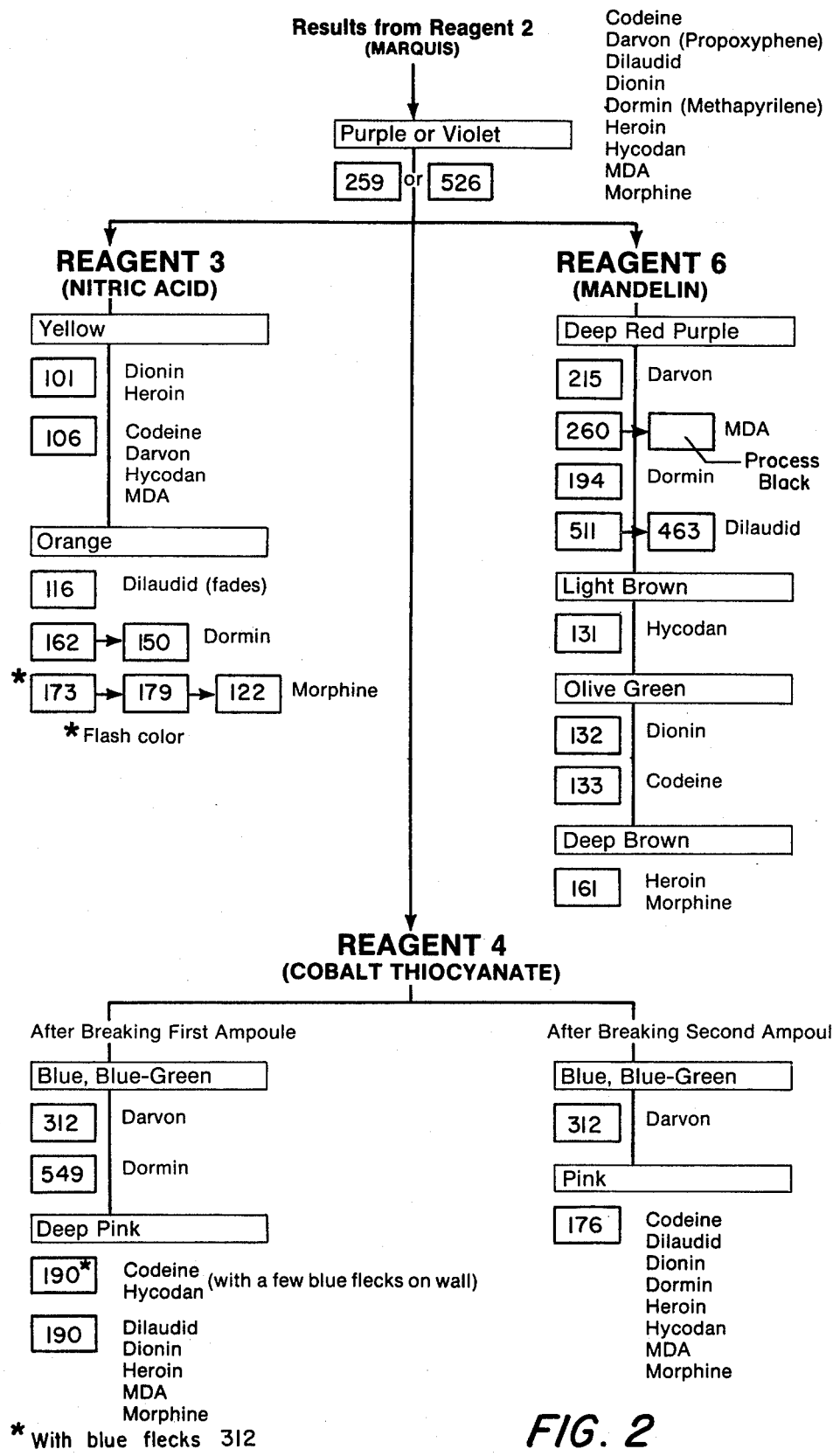
Figure 5:
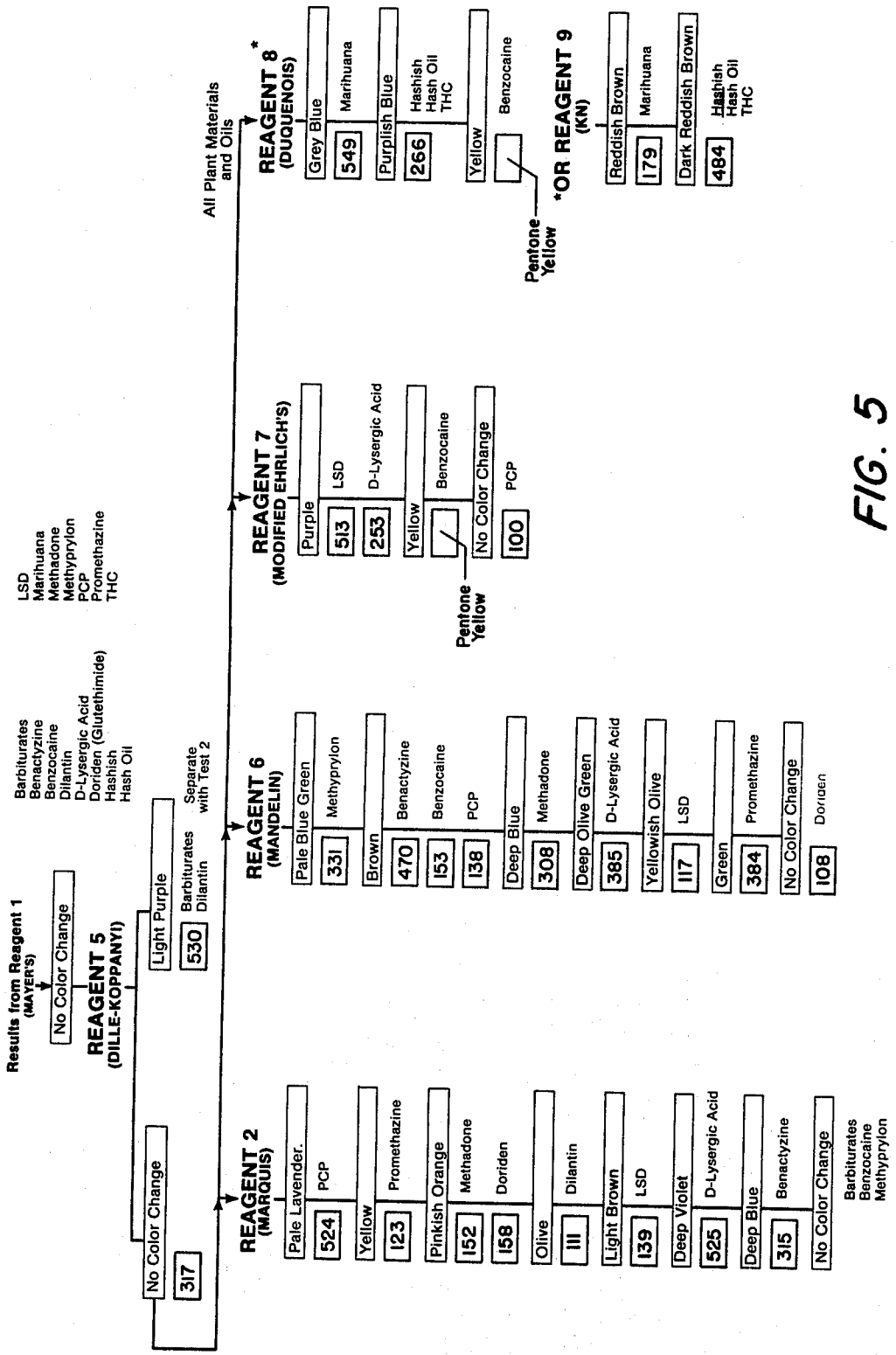

The test sequence in the process of the invention is shown in the accompanying drawings, in which:

FIG. 1 sets forth the initial test sequence, using first Mayer's reagent and then Marquis reagent, with reference to the subsequent charts to be referred to, according to the colors developed in these reagents;

FIG. 2 gives the test sequence to be used when the color with Marquis reagent is purple or violet;

FIG. 3 gives the test sequence to be used when the color with Marquis reagent is orange, red, or brown;

FIG. 4 gives the test sequence to be used when there is no color change with Mayer's reagent; and FIG. 5 gives the test sequence to be used when there is no color change with Mayer's reagent.

In all of these Figures, the precise colors produced in each test are identified in terms of Pantone color number as reported in the *Pantone Color Specifier* (PCS) or *Pantone Color & Black Selector* (PCBS) for precise identification of the color to be expected in each test.

In each of the color tests set forth, the sample of drug is within the range from about 1 to 5 mg and preferably from about 2 to about 3 mg, and the amount of each reagent is within the range from about 0.5 to about 0.55 cc, and preferably within the range from about 0.5 to about 0.52 cc. In two-reagent test units the amount of reagent is, of course, twice this amount.

The color is to be observed at a specific time interval, exactly one minute after mixing reagent and unknown substance. The color is then to be noted against a well lighted white background, in good light, so that the surrounding background neither masks nor changes the color produced. A very intense color can be viewed more readily if the tube is held nearly horizontally, so that the color can be viewed or compared through a thin film of solution.

Certain drugs always produce a fleeting or transient color when initially exposed to a given reagent. These are referred to in the charts as flash colors. A flash color may be characteristic of certain compounds, as characteristic as the final color that is more stable. Other compounds show a slow progression of color changes. Most of the opiates, for example, first produce an orange color in Marquis reagent, which changes within 20 to 40 seconds to a cherry red, and then turns a violet or reddish violet color.

Sometimes different salts of a given base produce a different final color. Mescaline hydrochloride changes from a deep green to an olive in Mandelin's reagent, while the sulfate changes from a deep green to a chocolate brown in the same reagent.

If the drug has a poor solubility in water, additional time and more thorough mixing may be required to obtain the color or response shown on the charts. The reaction of Mayer's reagent, a precipitating reagent for alkaloids, is much slower with bases than with water-soluble salts. Vigorous mixing is required, and a longer waiting time, to obtain a positive response in such cases.

The process of the invention is readily applied using a test kit composed of an array of the test reagents of FIGS. 1 to 6, separately sealed in glass ampoules, under vacuum. These ampoules are then correctly assembled for each reagent in plastic tubes. Where a reagent is composed of two parts, the second part is sealed into the cap of the unit. The reagents are present in the correct amount for a 2 to 3 mgm sample of the unknown substance. Samples of this size are normally no more than a few crystals of the drug, which can be held on a flat toothpick. The cap of the ampoule is removed, the sample is placed in the ampoule, the cap is replaced, and the ampoule then broken to release the reagent, and bring it into the contact with the sample. The test kit contains each of the reagents required by the test series of the charts shown in the drawings. Thus, by running quickly through the reagents provided, the test sequence can be followed from beginning to end within a matter of minutes, and of course the identification will be complete in many cases without having to proceed through the entire series, as will be apparent from a study of the charts.

All samples should be finely ground powders. Some materials are granular and need to be crushed. This can be done by placing the material between the folds of a folded piece of paper and then crushing with the back of a knife by pressing the material against a hard surface. Brown heroin is typically a rough granular material and not powdered. Procaine is usually like salt or coarse sugar in its granular form. The drug must be powdered or the color will not be distributed evenly throughout the reagent. In the case of cocaine hydrochloride, the pure material is quite fluffy and, if the amount held on the broad tip (3/16 inch) of a flat toothpick is not piled up, it is possible to have an insufficient sample. In the case of cocaine and cocaine derivatives, it is important to note that a blue flaky precipitate is formed with cobalt thiocyanate reagent, not a solution. The blue is very intense, and when first formed the mixture appears to be a solution. On standing beyond the recommended one minute color matching time the blue precipitate settles out, leaving a deep rose colored solution over the precipitate.

It is important to note that, with the exception of oils, the noted reagents give best results with dry solids rather than solutions. All solutions should be first allowed to dry so that the solids can be tested. Solutions would not only result, in the case of tests with concentrated sulfuric acid, in creating high temperatures of dilution of the sulfuric acid, but in the case of Mandelin's reagent, a different oxidation state of vanadium results, and this does not form the color responses stated. Cobalt thiocyanate reagent will respond to many more false positives when the suspect material is first wetted with water. Thus, drug solutions can be expected to respond in a like manner.

The following is a description of the process as outlined in the charts shown in the drawings:

As seen in the first chart of FIG. 1, the initial test is with Mayer's reagent. If a creamy white precipitate which may be gelatinous is formed, color No. 583, 20% color and 0% black (PCBS), Marquis reagent is next applied. If there is no creamy white precipitate formed, the test response is regarded as negative, and one proceeds to the fourth chart, shown in FIG. 5.

The reactions with Marquis reagent are shown in the chart of FIG. 1. If the color is purple No. 259 (PCS) or violet No. 526 (PCS) the test sequence of the second chart, shown on FIG. 2, is next applied.

If the color is orange No. 165 (PCS); red No. 179 (PSC); or brown No. 470 (PCS); the test sequence of the third chart shown on FIG. 3 is used.

If there is no color change with Marquis reagent, the test sequence of the fourth chart shown on FIG. 4 is used.

If there is no creamy white precipitate formed with Mayer's reagent, the test sequence of the fifth chart shown on FIG. 5 is used.

As seen in FIG. 2, a purple or violet color with Marquis reagent suggests codeine, Darvon (d-propoxyphene), dilaudid, dionin, dormin (methapyrilene), heroin, hycodan, MDA or morphine.

Using nitric acid reagent, a yellow color No. 101 (PSC) indicates dionin or heroin. A yellow color No. 106 (PCS) indicates codein, Darvon, hycodan or MDA. An orange color No. 116 (PCS) indicates dilaudid, whose presence can be reinforced by the fact that the color fades. An orange color No. 162 (PCS) intensifying to No. 150 (PCS) indicates dormin. A flash orange No. 173 (PCS) changing to orange red No. 179 (PCS) and then to yellow No. 122 (PCS) indicates morphine.

The cobalt thiocyanate reagent is in two parts: first, aqueous cobalt thiocyanate solution is added, and second, aqueous stannous chloride hydrochloric acid solution is added.

If after the addition of aqueous cobalt thiocyanate the color is blue No. 312 (PSC) the drug is Darvon. If the color is dark blue No. 549 (PCS), the drug is dormin. If the color is deep pink No. 190 (PCS) with a few flecks of blue No. 312 (PCS) the drug is codeine or hycodan. If the pink shade is No. 190 (PCS), the drug is dilaudid, dionin, heroin MDA or morphine.

If after the addition of aqueous stannous chloride in dilute hydrochloric acid present in ampoule No. 2 the color remains unchanged, No. 312 (PCS), the drug is Darvon. If the color fades to a pale pink No. 176 (PCS), the drug is codeine, dilaudid, dionin, dormin, heroin, hycodan, MDA or morphine.

With Mandelin reagent a deep red purple color No. 215 (PCS) indicates Darvon; a deep purple color No. 260 (PCS) turning to black indicates MDA. A lighter purple color No. 194 (PCS) indicates dormin. A dark purple color No. 511 (PCS) fading to a brown color No. 463 (PCS) indicates dilaudid.

A light brown color No. 131 (PCS) indicates hycodan.

An olive green color No. 132 (PCS) indicates dionin and a darker olive green No. 133 (PCS) indicates codeine.

A deep brown color No. 161 (PCS) indicates heroin or morphine.

By a comparison of the test results using all three reagents, nitric acid reagent, cobalt thiocyanate reagent, and Mandelin's reagent, it is possible to separate and distinguish each of these drugs one from the other, according to the specific colors given for individual drugs in the chart of FIG. 2.

An orange, red or brown color from the Marquis reagent test indicates that one should then proceed following the scheme of FIG. 3, and that the drug may be either one of the amphetamines, Demerol, DET, DMT, doxepin, mescaline, promazine or TMA.

With nitric acid reagent, a deep red color No. 222 (PCS) indicates TMA, and No. 207 (PCS) indicates mescaline. An orange yellow color No. 123 (PCS) indicates DET. A yellow color No. 394 (PCS) fading to No. 107 (PSC) indicates promazine. A strong orange color No. 144 (PCS) indicates DMT. No color change indicates the amphetamines, demerol or doxepin.

With Mandelin reagent, a yellow green color No. 577 (PCS) indicates amphetamines, and No. 583 (PCS) indicates promazine. A light olive green brown color No. 132 (PCS) indicates TMA. A deep brown color No. 194 (PCS) intensifying to No. 450 (PCS) indicates DET, and No. 363 (PCS) intensifying to No. 469 (PCS) or 385 (PCS) indicates mescaline. A dark brown No. 469 (PCS) indicates mescaline sulfate, and an olive green No. 385 (PCS) indicates mescaline hydrochloride. A deep reddish orange color No. 180 (PCS), indicates DMT and No. 160 (PCS) indicates doxepin. No color change, i.e. No. 108 (PCS), indicates demerol.

No color change from the Marquis reagent directs one to the test scheme on FIG. 4, and suggests one of antipyrine, cocaine, dibucaine, lidocaine, phendimetrazine, procaine or tetracaine.

The cobalt thiocyanate reagent is in two parts, first aqueous cobalt thiocyanate, and second aqueous stannous chloride in dilute hydrochloride acid.

A blue or blue green color No. 312 (PCS) with cobalt thiocyanate indicates cocaine, dibucaine, procaine or tetracaine. These are separately distinguished after addition of the second reagent. A deep pink coloration No. 190 (PCS) in which there are flecks of a blue green color No. 312 (PCS) indicates lidocaine. A deep pink color No. 190 (PCS) without blue flecks indicates antipyrine or phendimetrazine.

To the test solution there is then added the second reagent. If the color remains the same No. 312 (PCS) antipyrine or cocaine is suggested. If the color changes to pink, No. 176 (PCS) in which there are flecks of blue No. 312 (PCS) dibucaine or lidocaine is suggested. Color No. 176 (PCS) without blue flecks indicates phendimetrazine, procaine or tetracaine.

With Mandelin's reagent, a deep orange color No. 138 (PCS) indicates procaine or tetracaine. A yellowish orange color No. 123 (PCS) indicates dibucaine. A deep green flash color No. 362 (PCS) fading to light green No. 358 (PCS) indicates antipyrine. A purple red flash color No. 194 (PCS) changing to light green No. 366 (PCS) indicates lidocaine. No color change, i.e. yellow No. 108 (PCS) indicates phendimetrazine.

With Duquenois reagent, a light greenish yellow color No. 101 (PCS) indicates procaine. A yellow color No. 108 (PCS) indicates antipyrine. No color change indicates dibucaine, lidocaine, phendimetrazine or tetracaine.

Thus, it is possible to individually distinguish each of these drugs by this series of three test reagents.

No creamy white gelatinous substance being produced with Mayer's reagent directs one to follow the fourth test sequence shown on FIG. 5, and indicates barbiturates, benactyzine, benzocaine, dilantin, D-lysergic acid, doriden (glutethimide), hashish, hash oil, LSD, marihuana, methadone, methprylon, PCP, promethazine or THC.

The first reagent is the two-part Dille-Koppanyi reagent. A light purple color, No. 53 (PCS), formed after addition of the second part No. 530 (PCS) indicates either barbiturates or dilantin, which then can be distinguished using Marquis reagent in subsequent testing according to the Scheme on FIG. 5.

With Marquis reagent, a pale lavender color No. 524 (PCS) indicates PCP. A yellow color No. 123 (PCS) indicates promethazine. An orange color No. 152 (PCS) indicates methadone; a pinkish orange No. 158 (PCS) indicates doriden, an olive green color No. 111 (PCS) dilantin. A light brown color No. 139 (PCS) indicates LSD. A deep violet color No. 525 (PCS) indicates D-lysergic acid, and a deep blue color No. 315 (PCS) indicates benactyzine. No color change suggests either a barbiturate, benzocaine or methprylon. The lack of response of the barbiturates to this reagent separates it from dilantin while benzocaine and methyprylon are separated by their color responses to Mandelin reagent.

With Mandelin reagent, a pale green blue color No. 331 (PCS) indicates methprylon. A dark brown color No. 470 (PCS) indicates benactyzine, a light brown No. 153 (PCS) benzocaine, and pale orange No. 138 (PCS) PCP. A deep blue color No. 308 (PCS) indicates methadone. A deep olive green color No. 385 (PCS) indicates D-lysergic acid. A yellowish olive or mustard color No. 117 (PCS) indicates LSD. A green color No. 384 (PCS) indicates promethazine. No color change No. 108 (PCS) indicates doriden, which can be detected with Marquis reagent.

With modified two-part Ehrlich's reagent, a deep purple color No. 513 (PCS) indicates after addition of the second part LSD and a reddish purple No. 253 (PCS) after addition of the second part indicates D-lysergic acid. A yellow color, Pantone yellow, indicates benzocaine, and no color change, i.e. No. 100 (PCS) after addition of the second part indicates PCP.

With the two-part Duquenois reagent, a gray blue color No. 549 (PCS) after addition of the second part indicates marihuana. A purplish blue color No. 266 (PCS) after addition of the second part indicates hashish, hash oil or THC. A yellow color Pantone yellow after addition of the second part indicates benzocaine.

An alternative to Duquenois reagent for testing all materials suspected of being marihuana or one of its derivatives such as hashish, hashish oil or purified THC is the two-part KN reagent. Using this reagent, a reddish-brown color, No. 179 (PCS) forms after addition of the second part, and, if the color is distributed in both the aqueous layer on top and in the solvent layer below it indicates the presence of marihuana or one of its derivatives. A dark reddish-brown color, No. 484 (PCS) after addition of the second part indicates hashish, hash oil or THC.

Thus, as is apparent it is possible using the test sequences of the Figures to identify specifically without danger of false positives all of the commonly encountered drugs.

The reagents used in the test sequence of the invention are known reagents prepared by conventional procedures. For convenience of reference, the following preparatory procedures are given:

| Reagents | Formulation |
|---|---|
| Mayer's | Dissolve 38 grams of mercuric chloride in water; add 96 grams of potassium iodide. When scarlet precipitate is redissolved add water to make one gallon. |
| Marquis | Add 60 mls of 37% formaldehyde solution to 9 lbs of concentrated sulfuric acid |
| Nitric Acid | Concentrated Nitric Acid (70 to 71% HNO$_3$) |
| Cobalt Thiocyanate | (1) Dissolve 76 grams cobalt thiocyanate in one gallon of water. |
|  | (2) Dissolve 150 grams of stannous chloride dihydrate and 300 mls of concentrated hydrochloric acid in one gallon of water |
| Dille-Koppanyi | (1) Dissolve 2.8 grams of cobaltous acetate tetrahydrate and 7.6 mls of glacial acetic acid in 700 mls water, add isopropanol to make one gallon. |
|  | (2) Dilute 190 mls of isopropylamine to one gallon with isopropanol |
| Mandelin | Dissolve 22 grams of ammonium vanadate in 9 lbs of concentrated sulfuric acid |
| Modified Ehrlich's | (1) Dissolve 190 grams of paradimethylamino-benzaldehyde in one gallon of isopropanol |
|  | (2) Concentrated hydrochloric acid |
| Duquenois | (1) Dissolve 76 grams of vanillin and 19 mls of acetaldehyde in one gallon of isopropanol. |
|  | (2) Concentrated hydrochloric acid. |
| KN | (1) 12 grams Fast Blue B Salt suspended in one gallon trichlorethylene |
|  | (2) Dissolve 400 grams of sodium hydroxide pellets in one gallon of water |

All reagents are analytical grade reagents. One-half (0.5) ml of each reagent is vacuum sealed in each ampoule, and ampoule No. 1 is the bottom ampoule and ampoule No. 2 is the top ampoule in a two-part reagent kit.

The reference to "reagent" in the specification and claims is to the reagent prepared as above and used as indicated.

Having regard to the foregoing disclosure, the following is claimed as the inventive and patentable embodiments thereof.

1. A process for the presumptive identification of narcotics and drugs of abuse which comprises applying to a sample of the drug in an amount within the range from about 2 to about 3 mg in the sequence stated:
 (1) from about 0.5 to about 0.55 ml Mayer's reagent and then
 (2) in the event a creamy white precipitate forms, applying Marquis reagent; and then
  (a) in the event a purple color No. 259 (PC) or violet color No. 526 (PCS) forms, applying the test sequence of FIG. 2;
  (b) in the event an orange color No. 165 (PCS) forms, a red color No. 179 (PCS) forms, or a brown color No. 470 (PCS) forms, applying the sequence of FIG. 3; and
  (c) in the event there is no color change, applying the sequence of FIG. 4; and
 (3) in the event there is no precipitate with Mayer's reagent, applying the sequence of FIG. 5; and thereby identifying the drug according to the color changes produced in the test sequences applied.

2. A process in accordance with claim 1 in which a purple color No. 259 (PCS) or violet color No. 526 (PCS) is obtained in the test with Marquis reagent, and the following test sequence is then applied to separate sub-samples of the unknown material:
 (1) adding nitric acid reagent and noting the color;
 (2) adding Mandelin reagent and noting the color; and (3) adding cobalt thiocyanate reagent and noting the color.

3. A process in accordance with claim 1, in which an orange, red or brown color is obtained with Marquis reagent, and the following test sequence is then applied to separate sub-samples of the unknown material:
  (1) adding nitric acid reagent and noting the color; and
  (2) adding Mandelin reagent and noting the color.

4. A process in accordance with claim 1 in which no color change is obtained with Marquis reagent, and the following test sequence is then applied to separate sub-samples of the unknown material:
  (1) adding cobalt thiocyanate reagent and noting the color;
  (2) adding Mandelin reagent and noting the color; and
  (3) adding Duquenois reagent and noting the color.

5. A process according to claim 1, in which no precipitate is obtained after addition of Mayer's reagent, and the following test sequence is applied to separate sub-samples of the unknown material:
  (a) adding Dille-Koppanyi reagent and noting the color; and then, if there is no color change:
  (b) adding Marquis reagent and noting the color;
  (c) adding Mandelin reagent and noting the color;
  (d) adding modified Ehrlich's reagent and noting the color; and
  (e) adding Duquenois reagent and noting the color.

6. A process according to claim 1, in which no precipitate is obtained after addition of Mayer's reagent, and the following test sequence is applied to separate sub-samples of the unknown material:
  (a) adding Dille-Koppanyi reagent and noting the color; and then, if there is no color change:
  (b) adding Marquis reagent and noting the color;
  (c) adding Mandelin reagent and noting the color;
  (d) adding modified Ehrlich's reagent and noting the color;
  (e) adding KN reagent and noting the color.

* * * * *